United States Patent [19]

Komisaruk et al.

[11] Patent Number: 5,426,099
[45] Date of Patent: Jun. 20, 1995

[54] PROCESS FOR INDUCING ANALGESIA, PEPTIDES AND THERAPEUTIC COMPOSITIONS

[75] Inventors: Barry R. Komisaruk, Maplewood; Frank Jordan, Chatham, both of N.J.

[73] Assignee: Rutgers, The State University of New Jersey, New Brunswick, N.J.

[21] Appl. No.: 786,529

[22] Filed: Nov. 1, 1991

Related U.S. Application Data

[63] Continuation-in-part of Ser. No. 407,545, Sep. 15, 1989, abandoned.

[51] Int. Cl.$^6$ .................. A61K 38/00; C07K 5/00; C07K 7/00; C07K 14/00
[52] U.S. Cl. ..................... 514/13; 514/12; 514/14; 530/324; 530/326; 530/327; 530/300
[58] Field of Search .................. 514/12, 13, 14; 530/324, 326, 327, 300, 315

[56] References Cited

U.S. PATENT DOCUMENTS 4,237,046  12/1980  Podanszky .................. 530/327

OTHER PUBLICATIONS

Komisaruk et al., Annal.-New York Academy of Science, v. 527, 1988, pp. 650–654.

*Primary Examiner*—Jill Warden
*Assistant Examiner*—A. M. Davenport
*Attorney, Agent, or Firm*—Leroy G. Sinn

[57] ABSTRACT

Peptides having two or more amino acid residues in the sequence of the amino acid residues of vasoactive intestinal peptide (VIP) segment 11–28, analogs and derivatives thereof and pharmaceutically acceptable salts thereof are provided which are characterized by inducing analgesia by delivery to the central nervous system when administered to a mammal. Also provided is a method of inducing analgesia by delivery to the central nervous system using direct or indirect routes to administer VIP peptide segment 11–28, peptides having two or more amino acids of sequence of the VIP peptide segment, analogs and derivatives thereof and pharmaceutically acceptable salts thereof. Additionally are provided analgesic pharmaceutical compositions of said peptides, analogs and derivatives thereof or pharmaceutical salts thereof and a pharmaceutically acceptable carrier therefore.

10 Claims, 6 Drawing Sheets

PROCESS FOR INDUCING ANALGESIA, PEPTIDES AND THERAPEUTIC COMPOSITIONS

CROSS-REFERENCE TO RELATED APPLICATION

This application is a continuation-in-part of U.S. application Ser. No. 07/407,545, filed Sep. 15, 1989, and now abandoned.

TECHNICAL FIELD

This invention provides a process for inducing analgesia in mammals by the delivery to the central nervous system of one or more VIP (vasoactive intestinal peptide) peptide segments, analogs thereof, derivatives thereof, and pharmaceutically acceptable salts thereof; novel VIP peptide segments, analogs thereof, derivatives thereof, and pharmaceutically acceptable salts thereof which induce analgesia in mammals through the central nervous system when administered thereto; and analgesic pharmaceutical compositions thereof.

BACKGROUND ART

Vasoactive intestinal peptide (VIP) is known to exist in the small intestine, reproductive system, and central nervous system. It has been isolated from the small intestine of the hog and from the intestine of other animals, including the chicken.

The amino acid sequence of VIP peptide derived from the intestine of the hog has been described as having the following amino acid sequence:

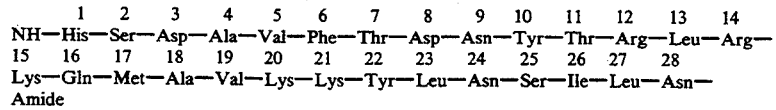

The conventional abbreviations for amino acids are the following:

| Amino Acid | Abbreviation |
|---|---|
| alanine | Ala |
| arginine | Arg |
| asparagine | Asn |
| aspartic acid | Asp |
| cysteine | cys |
| glutamic acid | Glu |
| glutamine | Gln |
| glycine | Gly |
| histidine | His |
| isoleucine | Ile |
| leucine | Leu |
| lysine | Lys |
| methionine | Met |
| norleucine | Nle |
| phenylalanine | Phe |
| proline | Pro |
| serine | Ser |
| threonine | Thr |
| tryptophan | Trp |
| tyrosine | Tyr |
| unknown or other amino acid | Xaa |
| valine | Val |

The amino acid units in VIP derived from animals are in the L-form.

VIP derived from other animals can differ somewhat in amino acid sequence. For example, VIP derived from the intestine of chicken varies from the above amino acid sequence of VIP derived from hog intestine as follows:
 a serine residue in position 11,
 a phenylalanine residue in position 13,
 a valine residue in position 26 and
 a threonine residue in position 28.

It has been reported that VIP, e.g., VIP (hog) as described above, has systemic vasodilator activity. The effects of VIP and/or its analogs include systemic hypotension (European Patent Publication No. 0 241 926 A2) and increases cardiac output on intravenous infusion. VIP and/or its analogs have been reported to increase hepatic arterial blood flow and blood sugar levels, and to have the ability to bring about a bronchodilatory action (U.S. Pat. No. 4,734,400) and relaxation of gut smooth muscle, as well as stimulation of colonic motility, anti ulcer action, and the output of bicarbonate from intestinal secretion. VIP and/or its analogs also stimulate tear secretion (U.S. Pat. No. 4,745,100), hairgrowth (European Patent Publication No. 0 225 639 A2), vaginal lubrication (PCT/US87/03038) and increase in pulse rate and cutaneous flushing (PCT/US87/03038). It therefore appears to be useful in treatment of hypertension and peripheral vascular disease on parenteral administration, and as a bronchodilator on aerosol or parenteral administration (U.S. Pat. No. 4,737,487).

The following is a list of reported actions of VIP:

| ACTION | SITE OF ACTION | SPECIES | AUTHOR | YEAR |
|---|---|---|---|---|
| cardiac output+ | systemic | dog | Said, Mutt | 75 |
| respiratory stimulation | systemic | dog | Said, Mutt | 75 |
| hyperglycemia | systemic | dog | Said, Mutt | 75 |
| cyclic AMP+ | pancreatic cells | guinea pig | Robberecht+ | 76 |
| blood pressure− | systemic | dog | Said, Mutt+ | 77 |
| arterial blood flow+ | systemic | dog | Said, Mutt+ | 77 |
| smooth muscle relaxation | stomach | rat | Said, Mutt+ | 77 |
| smooth muscle relaxation | trachea | guinea pig | said, mutt+ | 77 |
| smooth muscle motility+ | colon | rat | Said, Mutt+ | 77 |
| water flow+ | colon | rat | Waldman+ | 77 |
| cyclic AMP+ | brain (amygdala) | rat | Quik+ | 79 |
| cyclic AMP+ | mononuclear cells | human | Ottaway+ | 83 |
| ACTH, endorphin release | pit. tumor cells | mouse | Westendorf+ | 83 |
| intraocular pressure− | eye | rabbit | Mittag+ | 87 |

-continued

| ACTIONS OF VIP | | | | |
|---|---|---|---|---|
| ACTION | SITE OF ACTION | SPECIES | AUTHOR | YEAR |
| adenylate cyclase+ | arterial cells | bovine | Huang+ | 84 |
| glycogenolypis+ | cortical slices | mouse | Magistretti+ | 84 |
| vasodilation 30 | brain arteries | human | Suzuki+ | 84 |
| thyroid hormone secretion | systemic | mouse | khren | 85 |
| bronchodilation | bronchi | human | Palmer+ | 86 |
| neuronal hyperpolarization | Schwann cell | squid | Evans+ | |
| amylase release+ | colonic tumor | rat | Pandol+ | 86 |
| cyclic Amp+ | gastric mucosa | guinea pig | Sutliff+ | 86 |
| pepsinogen secretion+ | gastric mucosa | guinea pig | Sutliff+ | 86 |
| hair growth+ | skin | mouse | Yanaihara+ | 87 |
| lubrication+ | vagina | human | Fahrenkrug+ | 88 |
| chloride secretion+ | colonic cells | human | McCabe+ | 88 |
| blood flow+ | genital tract | human | Fahrenkrug+ | 88 |
| blood flow+ | heart | dog | Smitherman+ | 88 |
| renin secretion rate+ | kidney | dog | Porter+ | 88 |
| neuronal survival+ | spinal cord cult. | mouse fet. | Brenneman | 88 |
| REM sleep+ | brain (IV vent.) | cat | Drucker-Colin+ | 88 |
| somatostatin release+ | dienceph. cells | rat | Reichlin | 88 |
| amylase release+ | pancreatic acini | guinea pig | Musso+ | 88 |
| tear secretion+ | eye | rabbit | Gilbard+ | 88 |
| progesterone secretion+ | ovarian granulosa | hen | Johnson+ | 88 |
| androgen secretion+ | ovarian granulosa | hen | Johnson | 88 |
| arterial relaxation | uterus | guinea pig | Morris+ | 89 |

+ = Stimulation
− = Inhibition

Additionally, it has been reported that various VIP fragments, analogs and derivatives have various pharmacological activities.

It has also been reported that the intact VIP induced analgesia through the central nervous system when administered to rats directly into the periaqueductal gray matter (Sullivan, T. L. and A. Pert, [1981]. Soc. Neurosci. Abst. 7:504) or to the intrathecal space of the lumbo-sacral spinal cord (Komisaruk, B. R., C. Banas, S. B. Heller, B. Whipple, G. F. Barbato, and F. Jordan [1988] [Ed. S. I. Said and V. Mutt]. Ann. N.Y. Acad. Sci. 527:650–654). However, one study found that intrathecal injection of VIP reduced reaction time on a nociceptive test (Cridland, R. A. and J. L. Henry [1988]. Neuropeptides 11: 23–32).

It is desired that substantially smaller peptide segments of VIP analogs, derivatives or salts thereof be found which would induce analgesia through the central nervous system when administered to mammals. Such peptide segments would represent a substantial reduction in cost thereof and would provide other advantages, e.g., accessibility to the central nervous system, in view of the reduced length of the amino acid sequence of the peptide and molecular weight.

SUMMARY OF INVENTION

Provided by this invention are processes for inducing analgesia in mammals through delivery to the central nervous system of an effective amount of VIP 11–28 peptide segment, effective and pharmaceutically acceptable analogs and derivatives thereof, pharmaceutically acceptable salts of said peptides or combinations thereof. Also provided are peptides having a reduced length sequence of said VIP 11–28 peptide segment, wherein the length of said sequence is two or more amino acid residues, effective and pharmaceutically acceptable analogs and derivatives thereof and pharmaceutically acceptable salts thereof, or combinations thereof which provide effective analgesia when delivered to the central nervous system by direct, perispinal [intrathecal] or indirect [via blood stream] routes in an effective amount to a mammal in need of analgesia. Also provided by this invention are pharmaceutical compositions for inducing analgesia by delivery to the central nervous system when administered to a mammal in need of analgesia, which comprise an amount of a compound selected from the group consisting of VIP 11–28 peptide segment, effective and pharmaceutically acceptable peptides having a reduced length sequence of said VIP 11–28 peptide segment, wherein the length of said sequence is two or more amino acid residues, effective and pharmaceutically acceptable analogs and derivatives of said peptides, pharmaceutically acceptable salts of said peptides, or combinations thereof.

* Significantly greater than the saline group at the same test period (p <0.05, two-tailed multiple t-test).

*

* Also significantly greater than the morphine 25 mcg group at the same test period (p<0.05, two-tailed multiple t-test).

*,* Both VIP 11–28 25 mcge and morphine 25 mcg groups are significantly greater than the saline group at this test period (p <0.05, two-tailed, multiple t-test).

Figure 2:
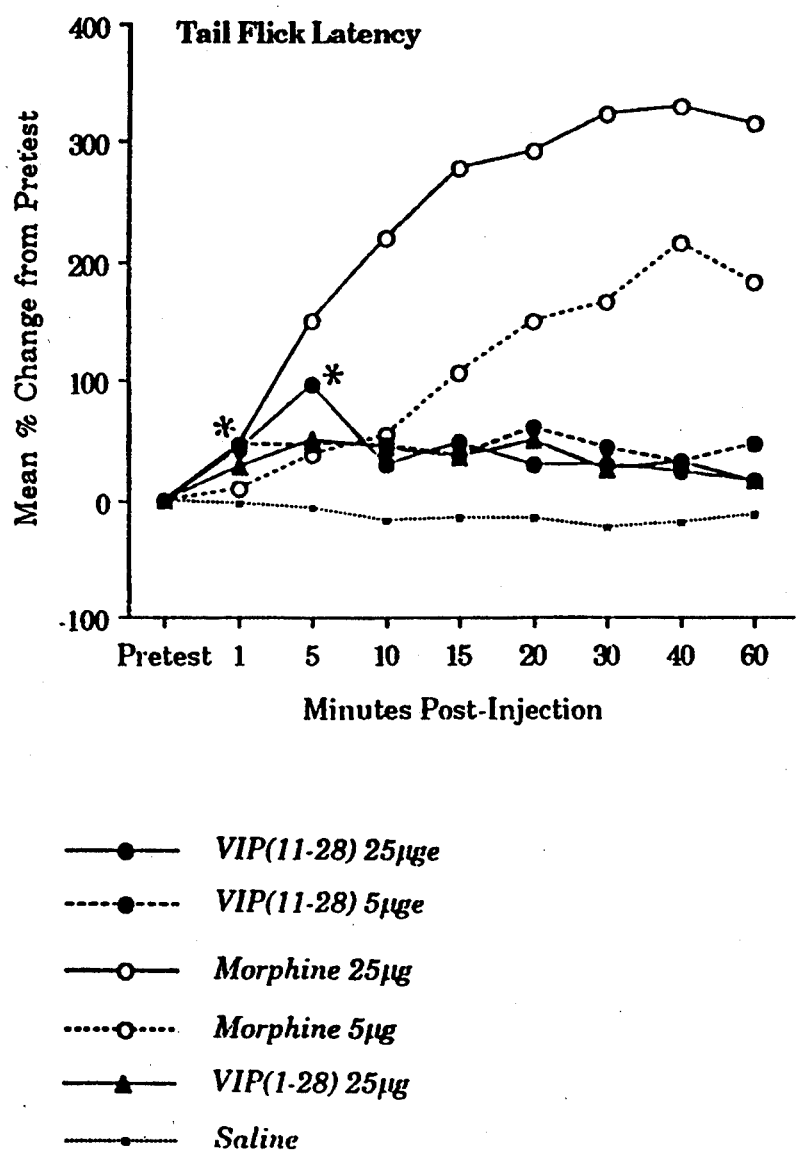

FIG. 2 is a graph showing the Mean % Change from Pretest at Minutes Post-Injection (intrathecal) of VIP 11–28, VIP 1–28 and morphine as compared to saline in the Tail Flick Latency Test.

, VIP 11–28 25 mcge group is significantly greater than the saline group (p<0.05, two-tailed, multiple t-test). The morphine 25 mcg group is significantly greater than all other groups at all points from 5–60 minutes (p<0.05, two-tailed, Duncan test), and the morphine 5 mcg group is significantly greater than saline at 15 min. and all other groups except morphine 25 mcg at all points from 30–60 min.

Figure 3:
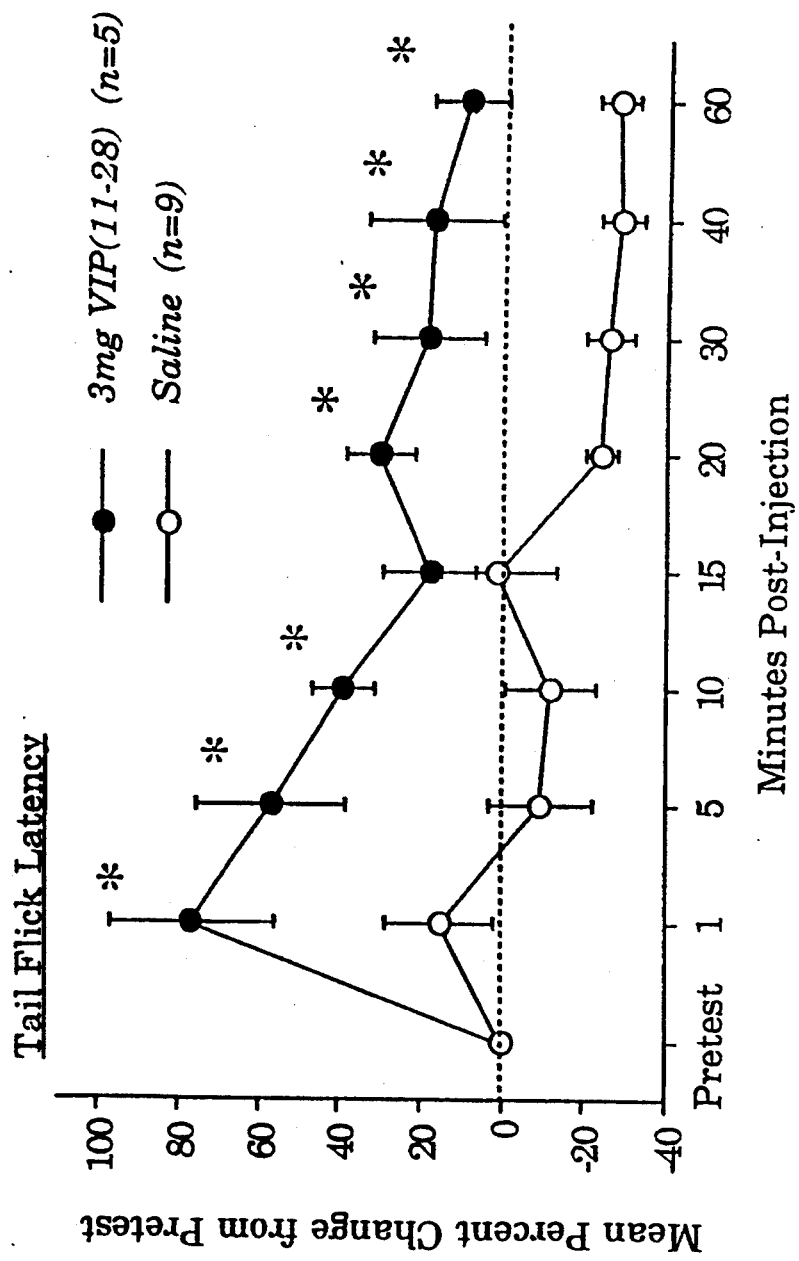

FIG. 3 is a graph showing the Mean Percent Change from Pretest at Minutes Post-Injection (intravenous) of VIP 11–28 as compared to saline in the Tail Flick Latency Test. It is noted that , indicates that 3 mg VIP 11–28 had a significantly greater effect than saline in elevating tail flick latency from 1–60 minutes with the exception of the test at 15 minutes (p<0.05, two-tailed Scheffe test).

Figure 4:
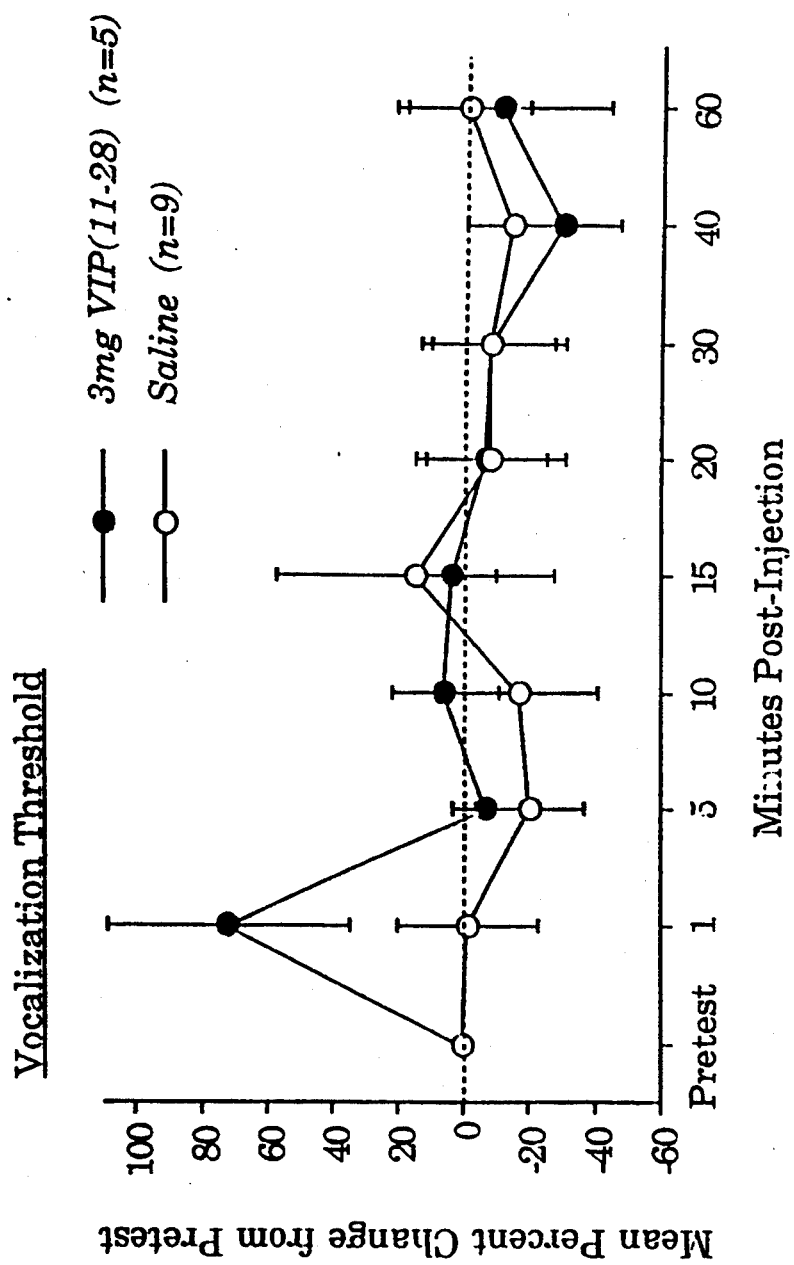

FIG. 4 is a graph showing the Mean Percent Change from Pretest at Minutes Post-Injection (intravenous) of VIP 11–28 as compared to saline in the Vocalization Threshold Test. The difference approached, but did not reach, significance under those conditions.

Figure 5:
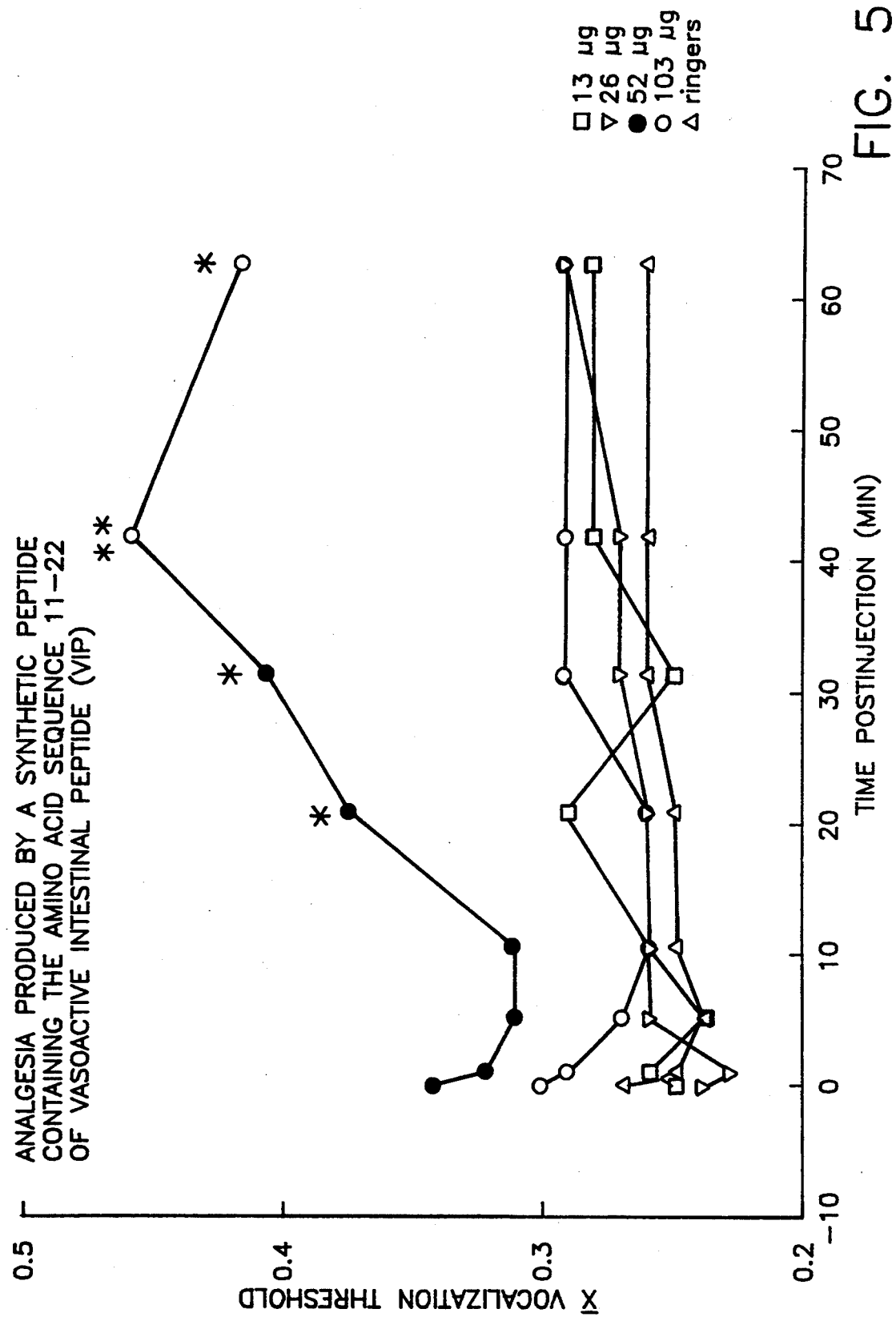

FIG. 5 is a graph showing analgesia produced by VIP 11–22 peptide in vocalization threshold test.

Figure 6:
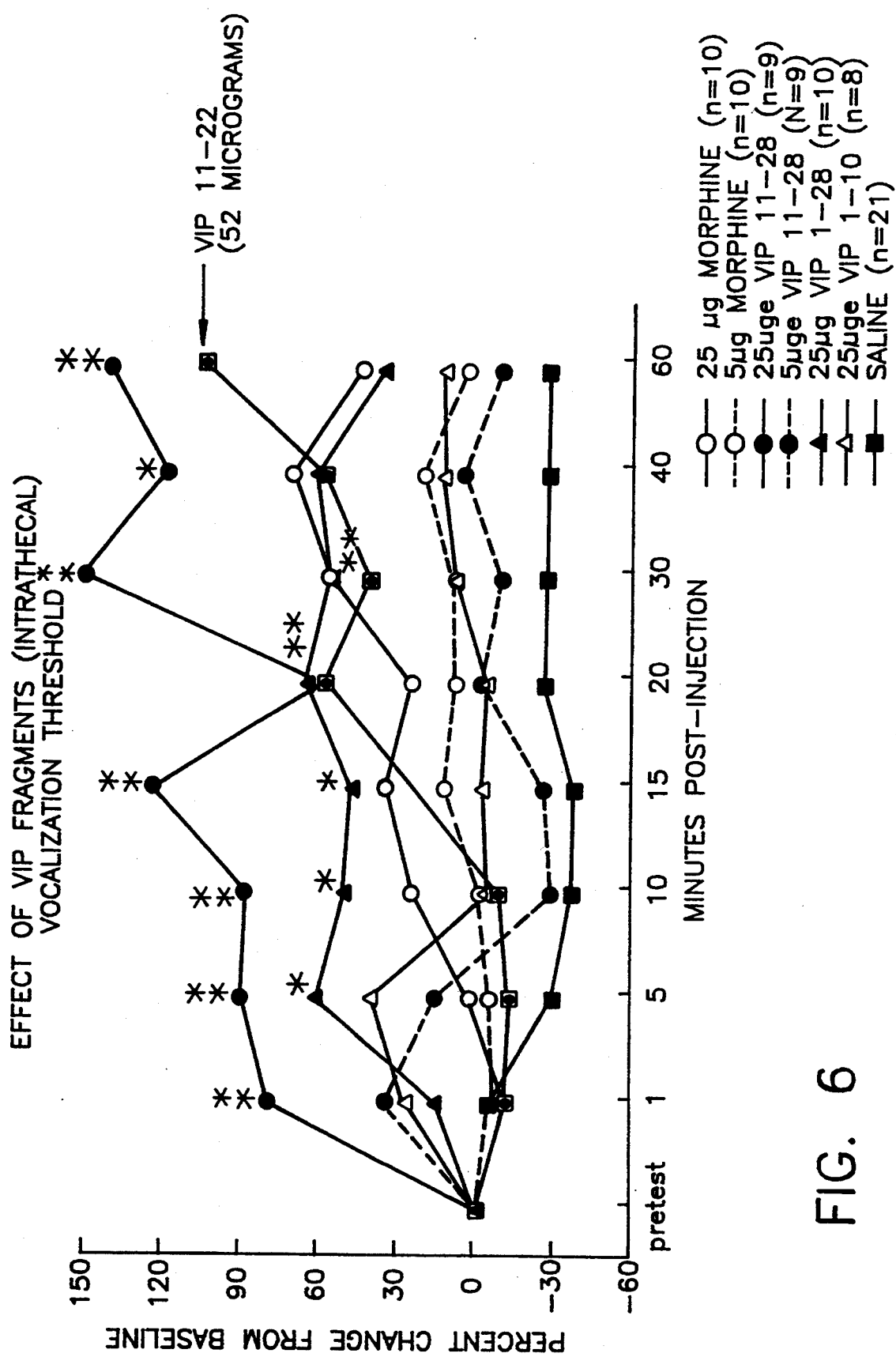

FIG. 6 is a graph showing analgesia produced by VIP peptides compared to controls in voocalization threshold test.

DETAILED DESCRIPTION OF THE INVENTION AND THE PREFERRED EMBODIMENTS

VIP occurs naturally in the tissues of the small intestine of animals, for example, in the intestines of hog and chicken, and also in the reproductive tract and central nervous system of mammals, including humans. The isolation and purification of VIP from the intestinal tissues has been previously described.

VIP has also been produced following known peptide synthesis methods.

The VIP 11–28 peptide segment can be provided by enzymatic cleavage of intact VIP at the peptide bond joining amino acid residues 10 and 11.

This cleavage can be accomplished by use of homogenate of the spinal cord as described by Barbato et al. 1988. Annals New York Academy of Sciences 527:582. Isolation and purification of the resulting VIP 11–28 peptide segment is also described by Barbato et al.

Substitutions can be made for certain amino acid residues of the VIP 11–28 peptide segment. Consideration can be taken in making the substitution that amino acids can be considered as members of different classes, which relationship is known.

In natural peptides, the amino acids are in the L-form. However, one or more of the amino acid residues can be in the D-form if such presence does not substantially interfere with the desired analgesic activity of the VIP 11–28 peptide segment.

The C-terminus of the peptides or analogs and derivatives thereof, which are the subject of the present invention, may be in the form of the acid (—OH); an ester, for example an alkyl ester, especially a ($C_1$–$C_4$)-alkyl ester, e.g. the methyl ester, (—OCH$_3$); the hydrazide (—N-H—NH$_2$); or an amide, usually the unsubstituted amide (—NH$_2$). Preferably the C-terminus is in the form of the unsubstituted amide.

The N-terminus of the peptides or analogs and derivatives thereof, which are the subject of the present invention, may be in the form of the unsubstituted amine (—NH$_2$) or protected amine (—NHR) wherein R represents, for example, acetyl or tert.-butyloxycarbonyl, RHN—Tyr—NR$_1$, wherein R is as above defined and R$_1$ is selected from hydrogen or a lower alkyl, preferably methyl, RHN—Asp—Asn—Tyr—NR$_1$, wherein R and R$_1$ have the same definitions as set out above, and the primary amide group of Asn can be substituted with a biocompatible group R$_2$ which can be a methyl or other lower alkyl groups or a carbohydrate such as fructose, mannose, galactose or N-acetylglucosamine or the like.

Acid addition salts may be, for example, salts with inorganic acids such as, for example, hydrochloric acid, hydrobromic acid, orthophosphoric acid, sulfuric acid or the like, or organic acids such as, for example, methanesulfonic acid, toluenesulfonic acid, acetic acid, trifluoroacetic acid, propionic acid, lactic acid, citric acid, tartaric acid, fumaric acid, malic acid, succinic acid, salicylic acid or acetylsalicylic acid or the like.

As set forth above, VIP (hog) 11–28 peptide segment has the following sequence:

```
     11   12   13   14   15   16   17   18   19   20   21   22   23   24
NH—Thr—Arg—Leu—Arg—Lys—Gln—Met—Ala—Val—Lys—Lys—Tyr—Leu—Asn—
     25   26   27   28
    Ser—Ile—Leu—Asn-Amide
```

Also, as noted above, some other 11–28 peptide segments of natural VIP peptides differ somewhat from the above sequence of VIP (hog) 11–28 peptide segment. The VIP (chicken) 11–28 peptide segment has the following differences:

11 residue is Ser
13 residue is Phe
26 residue is Val
28 residue is Thr

Other replacements of amino acids of the above VIP (hog) 11–28 peptide sequence can be made by equivalent amino acids of the same class or in the case in which an amino acid of the sequence can be grouped into two or more classes, replacement may be made from one or more of those classes.

Replacement amino acids may be naturally occurring amino acids, i.e. L-amino acids, or amino acids in the D- or DL-form, so long as the desired activity and other properties are retained. Activity of the VIP 11–28 segment, for example, could require or be related to a highly ordered arrangement of amino acid residues of the peptide segment, e.g., a helical structure of certain sequential amino acid residues. In such case, the replacement amino acid is selected to maintain such structure-activity relationship. Substitution of a D-amino acid for a L-amino acid residue of a helical structure will interfere with that helical structure.

The VIP 11–28 peptide segments which are a subject of this invention can accordingly be represented by the following formula (letters are not used in the sense of single letter coding of amino acids):

```
   11  12  13  14  15  16  17  18  19 20 21 22 23  24
   X—A—B—C—D—E—F—G—H—I—J—K—L—M—N—
                 25 26 27 28
                 O—P—Q—U—Y
``` wherein X represents a hydrogen atom or an amine-protecting group,

A represents Thr, Ser or another hydroxy amino acid,

B represents Arg or another basic amino acid,

C represents Leu, Phe or another naturally occurring hydrophobic amino acid,

D represents Arg or another naturally occurring basic amino acid,

E represents Lys or another naturally occurring basic amino acid,

D or E also represents a naturally occurring non-basic amino acid,

F represents Gln or another naturally occurring carboxamido amino acid,

G represents Met or Nle,

H represents Ala or another naturally occurring hydrophobic amino acid,

I represents Val or another naturally occurring hydrophobic amino acid,

J represents Lys or another naturally occurring basic amino acid,

K represents Lys or another naturally occurring basic amino acid,

J or K also represents a naturally occurring non-basic amino acid,

L represents Tyr, another naturally occurring hydrophobic amino acid or D—Tyr,

M represents Leu or another naturally occurring hydrophobic amino acid,

L—M peptide bond can be N-alkylated, preferably N-methylated,

N represents Asn or another naturally occurring carboxamido amino acid,

O represents Ser or another naturally occurring hydroxy amino acid,

P represents Ile, Val or another hydrophobic amino acid,

Q represents Leu or another hydrophobic amino acid,

U represents Asn, another naturally occurring carboxy terminally amidated amino acid, or Thr Y represents the C-terminus in the form of the acid (—OH); form of an ester, for example an alkyl ester, especially a ($C_1$-$C_4$)-alkyl ester, preferably methyl ester (—$OCH_3$); form of the hydrazide (—$NHNH_2$), amide, unsubstituted (—$NH_2$) or mono N-alkylated, e.g., N-ethylamide, preferably unsubstituted; and pharmaceutically acceptable salts thereof.

The above peptide fragments can be represented by the following formula:

X—S—Y wherein S is the above defined peptide segment —A—B—C—D—E—F—G—H—I—J—K—L—M—N—O—P—Q—U— in which the sequence of said segment is reduced in length by 1–16 amino acid residues, the number of amino acid residues represented by said reduction in length can be 0–16 amino acid residues from the N-terminus and C-terminus, provided that the sum of the reductions in length of the amino acid sequence from the N-terminus and C-terminus, respectively, is at least one and does not exceed 16. X and Y have the definitions as set forth above.

A further subject of this invention are the effective and pharmaceutically acceptable VIP 11–28 peptide segment fragments selected from the following i.e., induce analgesia when delivered to the central nervous system when administered to a mammal: 11–27 (A-Q); 11–26 (A-P); 11–25 (A-O); 11–24 (A-N); 11–23 (A-M); 11–22 (A-L); 11–21 (A-K); 11–20 (A-J); 11–19 (A-I); 11–18 (A-H); 11–17 (A-G); 11–16 (A-F); 11–15 (A-E); 11–14 (A-D); 11–13 (A-C); 11–12 (A-12); 12–28 (B-U); 12–27 (B-Q); 12–26 (B-P); 12–25 (B-O); 12–24 (B-N); 12–23 (B-M); 12–22 (B-L); 12–21 (B-K); 12–20 (B-J); 12–19 (B-I); 12–18 (B-H); 12–17 (B-G); 12–16 (B-F); 12–15 (B-E); 12–14 (B-D); 12–13 (B-C); 13–28 (C-U); 13–27 (C-Q); 13–26 (C-P); 13–25 (C-O); 13–24 (C-N); 13–23 (C-M); 13–22 (C-L); 13–21 (C-K); 13–20 (C-J); 13–19 (C-I); 13–18 (C-H); 13–17 (C-G); 13–16 (C-F); 13–15 (C-E); 13–14 (C-D); 14–28 (D-U); 14–27 (D-Q); 14–26 (D-P); 14–25 (D-O); 14–24 (D-N); 14–23 (D-M); 14–22 (D-L); 14–21 (D-K); 14–20 (D-J); 14–19 (D-I); 4–18 (D-H); 14–17 (D-G); 14–16 (D-F); 14–15 (D-E); 15–28 (E-8); 15–27 (E-Q); 15–26 (E-P); 15–25 (E-O); 15–24 (E-N); 5–23 (E-M); 15–22 (E-L); 15–21 (E-K); 15–20 (E-J); 15–19 (E-I); 15–18 (E-H); 15–17 (E-G); 15–16 (E-F); 16–28 (F-U); 16–27 (F-Q); 16–26 (F-P); 16–25 (F-O); 16–24 (F-N); 16–23 (F-M); 16–22 (F-L); 16–21 (F-K); 16–20 (F-J); 16–19 (F-I); 16–18 (F-H); 16–17 (F-G); 17–28 (G-U); 17–27 (G-Q); 17–26 (G-P); 17–25 (G-O); 17–24 (G-N); 17–23 (G-M); 17–22 (G-L); 17–21 (G-K); 17–20 (G-J); 17–19 (G-I); 17–18 (G-H); 18–28 (H-U); 18–27 (H-Q); 18–26 (H-P); 18–25 (H-O); 18–24 (H-N); 18–23 (H-M); 18–22 (H-L); 18–21 (H-K); 18–20 (H-J); 18–19 (H-I); 19–28 (I-U); 19–27 (I-Q); 19–26 (I-P); 19–25 (I-O); 19–24 (I-N); 19–23 (I-M); 19–22 (I-L); 19–21 (I-K); 19–20 (I-J); 20–28 (J-U); 20–27 (J-Q); 20–26 (J-P); 20–25 (J-O); 20–24 (J-N); 20–23 (J-M); 20–22 (J-L); 20–21 (J-K); 21–28 (K-U); 21–27 (K-Q); 21–26 (K-P); 21–25 (K-O); 21–24 (K-N); 21–23 (K-M); 21–22 (K-L); 22–28 (L-U); 22–27 (L-Q); 22–26 (L-P); 22–25 (L-O); 22–24 (L-N); 22–23 (L-M); 23–28 (M-U); 23–27 (M-Q); 23–26 (M-P); 23–25 (M-O); 23–24 (M-N); 24–28 (N-U); 24–27 (N-Q); 24–26 (N-P); 24–25 (N-O); 25–28 (O-U); 25–27 (O-Q); 25–26 (O-P); 26–28 (P-U); 26–27 (P-Q); 27–28 (Q-U).

The peptides provided herein are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95% or more.

The peptides which are the subject of this invention may be prepared synthetically by methods known in the art for the peptide synthesis and in this regard reference is made, by way of illustration only, to the following literature:

(a) Y. S. Klausner and M. Bodanszky, Bioorg. Chem. (1973), 2, p. 354–362.

(b) M. Bodanszky, C. Yang Lin and S. I. Said, Bioorg. Chem. (1974), 3, p. 320–323.

(c) S. R. Pettit, "Synthetic Peptides", (Elsevier Scientific Publishing Co., 1976).

(d) Stewart and Young, "Solid Phase Peptide Synthesis" (W. H. Freeman and Co., 1969).

(e) E. Atherton, C. J. Logan and R. C. Sheppart, J. C. S. Perkin I, (1981) p. 583–546.

(f) E. Brown, R. C. Sheppart and B. J. Williams, J. C. S. Perkin I (1983), p. 1161–1167.

(g) M. Bodansky, "Peptide Chemistry, A Practical Textbook" (Springer Verlag, 1988).

A peptide which is the subject of this invention may, for example, be formed by the sequential coupling of appropriate amino acids or by the initial preparation and subsequent coupling of peptide subunits, themselves prepared in a stepwise manner; in either case either classical solution chemistry methods of peptide synthesis or solid phase procedures may be used.

The coupling reactions may be effected by, for example, activating the reacting carboxyl group of the ingoing amino acids, and reacting this with the amino group of the substrate unit. Details of suitable, optional activating and protecting (masking) groups and of suitable reaction conditions (for the coupling reactions and for the introduction and removal of protecting groups) giving, preferably, the minimum of racemization, may be found in the above-referenced literature.

Accordingly, the present invention further provides a process for the preparation of a peptide or analog of the present invention, which comprises coupling a suitable amino acid or amino acid sequence in which the carboxyl group is activated with an appropriate amino acid or amino acid sequence and repeating, if necessary, the coupling procedure until there is obtained a peptide comprising, in sequence, units selected from the amino acid residues 11 to 28 of VIP or an analog thereof in which one or more of the amino acid residues is replaced by an equivalent other amino acid, wherein, if desired or required, non-reacting functional groups are protected during the coupling procedure and, if desired, subsequently deprotected. Likewise, the other peptides utilized in the invention are made.

A polypeptide of the general formula X—S—Y may thus be prepared by reacting a reagent of the general formula

H—V—OH wherein V represents an amino acid or a partial radical sequence identical with the corresponding N-terminal amino acid unit, with a reagent of the general formula

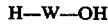

H—W—OH wherein W represents an amino acid unit or a partial radical sequence identical with that in the balance of the above-defined product peptide, the reagents H—V—OH and H—W—OH being optimally protected and/or activated when and as appropriate, followed if desired or required by one or more of the following: deprotection of the products, conversion of one carboxy terminus into another carboxy terminus, conversion of a free peptide into a salt thereof. For example, an appropriate peptide ester of the general formula

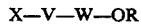

X—V—W—OR wherein X, V and W have the meanings given above and R represents, for example, an alkyl group and preferably an alkyl group having 1 to 4 carbon atoms, may be converted into an amide by reaction with ammonia.

Compounds of the general formulae H—V—OH, H—W—OH and X—V—W—OR may themselves be prepared by standard techniques analogous to those described above.

It will be appreciated that protected forms of a peptide or analog of the present invention are useful novel intermediates and form an aspect of the invention.

A peptide or analog of the present invention may also be prepared on a solid phase support, for example a polyamide or a polystyrene resin, using amino acids protected at the N-terminus, for example with the fluorenylmethyloxycarbonyl group or the t-butyloxycarbonyl group (t-boc) and with an appropriate protection of any side-chain functional groups. In specific illustration, synthesis is carried out using standard t-boc solid phase peptide synthesis methods on an Applied Biosystems 430A automated synthesizer in a stepwise manner (generally described by Merrifield, R. B., J. Am. Chem. Soc. 85, 2149 [1963] and employing p-methylbenzhydrylamine resin [substitution 0.5 mmol of resin, 0.82g]). This is a standard resin, commercially available, if a C-terminal amide is desired. As part of the structure proof for the fragment VIP 11–28, the entire VIP (1–28) was also synthesized at the same time to validate the synthetic procedure, since both syntheses originate with carboxy terminus. The synthetic VIP 1–28 was in every respect identical to commercially available material. The t-butyloxycarbonyl group for the N-terminus, and the groups in parentheses for the side chains were used: Arg (Tos, or p-toluenesulfonyl), Asp (O—Bzl, Bzl or benzyl), His(Tos, or p-toluenesulfonyl), Lys (Cl—Z, or 2-chlorobenzyloxycarbonyl), Ser(Bzl, or benzyl), Thr (Bzl, or benzyl), Tyr (Bzl, or benzyl; or 2,6-dichlorobenzyl).

The composition of the peptides were as follows (numbering from the N-terminus):

VIP 11–28

NH—Thr—Arg—Leu—Arg—Lys—Gln—Met—Ala—Val—Lys—Lys—Tyr—Leu—Asn—Ser—Ile—Leu—Asn—Amide

VIP 1–28

NH—His—Ser—Asp—Ala—Val—Phe—Thr—Asp—Asn—Tyr—Thr—Arg—Leu—Arg—Lys—Gln—Met—Ala—Val—Lys—Lys—Tyr—Leu—Asn—Ser—Ile—Leu—Asn—Amide The percentage of coupling after each cycle was monitored by the ninhydrin test (Kaiser, E. T. et al. Anal. Biochem. 34, 595 [1970]) and gave the following results (starting from the carboxy terminus): Asn28:99.9; Leu27:99.9; Ile26:99.7; Ser25:99.7; Asn24:99.9; Leu23:99.9; Tyr22:99.6; Lys21:99.7; Lys20:99.6; Val19:99.5; Ala18:99.7; Met17:99.6; Gln16:99.2; Lys15:98.8; Arg14:98.2; Leu13:98.8; Arg12:98.3; Thr11:99.4; Tyr10:99.7; Asn9:99.7; Asp8:99.6; Thr7:99.7; Phe6:99.6; Val5:99.6; Ala4:99.7; Asp3:99.6; Ser2:99.5; His1:99.7.

The amino acids at positions Asn28, Asn24, Gln16, Arg14, Arg12, Thr11, Asn9, Thr7, Val5, and Ala4 were double coupled.

As will be obvious to those practicing the art, other amino side chain protecting groups such as F-moc (9-fluorenylmethyloxycarbonyl) may also be used in place of t-butyloxycarbonyl groups. All amino acids protected at their amino termini with either one of these groups, or with others, are commercially available from a number of sources.

Cleavage of the peptide from the resin: the dried peptides (0.7–0.8 g) were treated with 8–9 ml of HF for one hour at 5° C. in the presence of ca. 0.8 ml anisole, 0.35 ml dimethylsulfide and 0.25 ml ethylene glycol to protect the amino acids from alkylation or oxidation.

Extraction of the peptide from the resin was accomplished as follows: After cleavage with HF, the crude peptide was washed with cold ether/mercaptoethanol (99:1 v/v, 3×10 ml) to remove anisole and by-products. Next, the peptide was extracted from the resin with 6 M guanidine HCl/1% mercaptoethanol (2×3 ml), the mixture was filtered. This procedure was repeated three times and the combined filtrates were frozen.

Purification was accomplished by gradient High Performance Liquid Chromatography with ultraviolet detection at 229 nm. Separations were performed on a Vydac C-18 column (22×250 mm), 300 A pores, 10 micrometer particle size. The gradient consisted of mobile phases A (0.1% trifluoroacetic acid in water) and B (0.087% trifluoroacetic acid in water/acetonitrile/isopropyl alcohol, 10/70/20 v/v/v). The protocol started with 10 min. isocratic elution at 100% A, followed by a shallow gradient for 40 min. to 60% B, followed by a sharp gradient for 5 min. to 95% B. The flow rate was 4 ml/min.

Amino acid analysis: two aliquots of 10 microliters each of the above peptides were subjected to amino acid analysis, along with two blanks, one for background contamination, the other used human serum albumin to test for completion of hydrolysis.

Amino acid composition of VIP and fragment 11-28

VIP 11-28

|  | Theory | Experiment |
|---|---|---|
| Asp/Asn | 2 | 2.2 |
| Ser | 1 | 1.1 |
| Glu/Gln | 1 | 1.1 |
| Thr | 1 | 0.9 |
| Ala | 1 | 1.1 |
| Val | 1 | 1.0 |
| Met | 1 | 0.9 |
| Tyr | 1 | 0.9 |
| Ile | 1 | 0.9 |
| Leu | 3 | 3.1 |
| Lys | 3 | 3.0 |
| Arg | 2 | 2.3 |

VIP 1-28

|  | Theory | Experiment |
|---|---|---|
| Asp/Asn | 5 | 5.1 |
| Ser | 2 | 1.4 |
| Glu/Gln | 1 | 1.1 |
| Thr | 2 | 1.7 |
| Ala | 2 | 2.1 |
| Val | 2 | 1.9 |
| Met | 1 | 1.1 |
| Tyr | 2 | 2.1 |
| Ile | 1 | 0.9 |
| Leu | 3 | 3.1 |
| Phe | 1 | 0.9 |
| His | 1 | 1.0 |
| Lys | 3 | 3.1 |
| Arg | 2 | 2.3 |

Derivatives of the above fragments that may show prolonged stability and/or enhanced bioactivity as analgesics a. amino terminally blocked: by introduction of NMeDAla to protect from amino exopeptidases. In general, the amino terminus of the peptides or analogs of the present invention may be in the form of the unsubstituted amine ($NH_2$) or protected amine (—NHR) where R represents, for example, acetyl, or tert-butyloxycarbonyl, RHN—Tyr—$NR_1$— wherein R is as above defined and $R_1$ is selected from hydrogen or a lower alkyl, preferably methyl, RHN—Asp—Asn—Tyr—$NR_1$— wherein R and $R_1$ have the same definitions as set out above and the primary amide group of Asn can be substituted with biocompatible, non-interfering groups, for example, with a methyl or other alkyl group, or carbohydrates such as fructose, mannose, galactose, N-acetylglucosamine or the like. Suitable acid addition salts for use in the processes of this invention may be made, for example, by use of hydrochloric acid, hydrobromide acid, orthophosphoric acid or sulfuric acid, or organic acids, such as for example methanesulfonic acid, toluene sulfonic acid, acetic acid, trifluoroacetic acid, propionic acid, lactic acid, citric acid, tartaric acid, fumaric acid, malic acid, maleic acid, succinic acid, salicylic acid, or acetylsalycilic acid.

b. carboxamido group terminally blocked; N-ethylamides to protect from carboxyterminal exopeptidases and deamidases. In general, the carboxy terminus of the peptides or analogs of the present invention may be in the form of the acid (—OH); an ester, for example an alkyl ester, especially a ($C_1$-$C_4$)-alkyl ester, preferably the methyl ester (—$OCH_3$); the hydrazide (—$NHNH_2$); or an amide, unsubstituted or mono N-alkylated. Preferably, the carboxy terminus is in the form of the unsubstituted amide.

c. The L—M peptide bond and any like bonds can be protected with a biocompatible, non-interfering group, as provided by N-methylation. N-methylation is provided by conventional means, for example, by reductive amination using sodium borohydride and formaldehyde.

The following are procedures followed in evaluating the peptides, analogs, derivatives and salts used in the therapeutic methods of this invention:

Intrathecal Catheterization

The catheter (PE 10 polyethylene tubing 7.5 cm length) is implanted surgically through the cisterna magna in 250 g female Sprague-Dawley rats to terminate in the intrathecal space of the lumbo-sacral region of the spinal cord. The rostral end is passed through a scalp incision and receives a removable plug. After at least one week recovery, the drug is injected over a 1 min. period in 5 microliters saline with a 5 microliter saline (Ringer's solution) flush. Analgesia testing commences immediately upon completion of the injection and at 5, 10, 20, 40 and 60 min. thereafter. For the procedure, the rat is placed in a cylindrical ventilated Plexiglas restrainer.

Analgesia Testing

The following tests have been used in rats to demonstrate analgesic activity of this composition. These tests, or minor variations thereof, are commonly used to ascertain analgesic effectiveness of pharmaceutical compositions (e.g.: Tang and Schoenfeld, 1978; Schmauss and Yaksh, 1984; Crowley et al., 1976; Steinman et al., 1983). All procedures have been approved by the Rutgers University Institutional Animal Care and Utilization Committee (IACUC).

Vocalization Threshold to Tail Shock

Electrical stimulation (100 millisecond trains of 60 Hz square waveform at three-second intervals ranging from 0.01 to 0.4 mA in 0.01 mA increments) is applied (under computer control using a Commodore 64C computer and a Coulbourn constant current stimulator) to the surface of the tail via two lengths of blunt 18-ga stainless steel tubing coated with conductive gel (Spectra 360 Electrode Gel; Parker Laboratories Inc., Orange, N.J. 07050) and taped to the midsection of the tail 2 cm apart, parallel to the axis of the tail. An ascending/descending method of limits is used to estimate the threshold (in mA) to induce vocalization. In this method, an observer records whether or not vocalization occurs in response to each shock. If an animal vocalizes at a particular current intensity, the current intensity is then reduced stepwise until a shock no longer elicits a vocalization response. Then the current is increased stepwise until the animal again vocalizes, and so on, until all mA values for 6 such inversions are obtained. The vocalization threshold estimate is the mean of these 6 values.

Tail-Flick-Latency to Radiant Heat

A radiant heat source (IITC Inc., Model 33, P.O. Box M551, 101 Landing Road, Landing, N.J. 07850) is mounted 8 cm above the tail and is applied 4 cm proximal to the tip of the tail. When the lightly restrained animal flicks its tail in response to the heat, a photocell circuit is broken and the latency is displayed automatically. The intensity of the thermal stimulus is adjusted to produce a baseline tail flick latency below 3 sec. The mean of three successive latency determinations taken 15 sec. apart is calculated as the data point. A maximum duration of 10 sec., at which the radiant heat is terminated, is employed to prevent tissue damage.

EXAMPLE 1 (VIP 11–28)

Vocalization Threshold Test (n=10)

Figure 1:
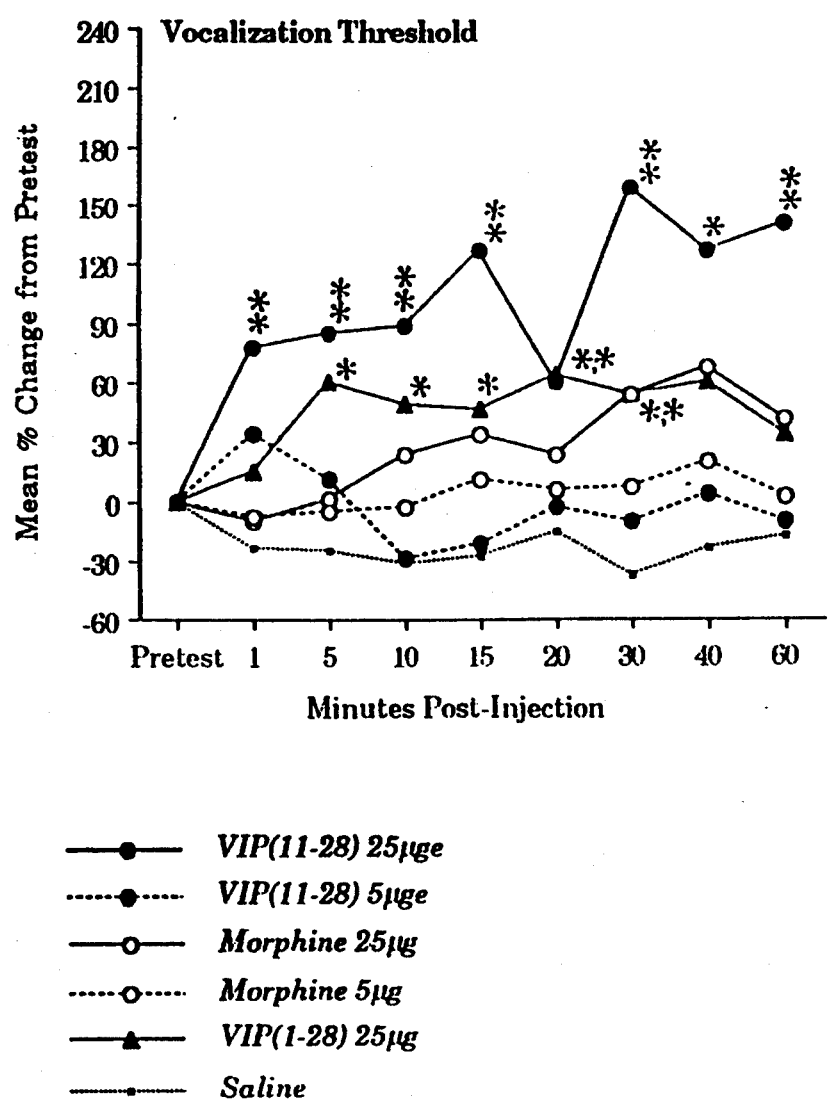
FIG. 1 is a graph showing the Mean % Change from Pretest at Minutes Post-Injection (intrathecal) of VIP 11–28, VIP 1–28 and morphine as compared to saline in the Vocalization Threshold Test. It is to be noted that at 30 min. the morphine 25 mcg. group is significantly greater than the saline group, while the VIP 11–28 25 mcge group is significantly greater than both the morphine and the saline groups.

The vocalization threshold to tail shock increased by 70% over baseline (pre-injection) levels by the first minute after the intrathecal injection of VIP 11–28 (molar quantity equivalent to 25 mcg VIP 11–28, hereafter referred to as 25 mcge [microgram equivalents]). This was significantly greater than the saline controls ($p < 0.05$, 2-tailed, multiple t-tests). The vocalization threshold remained significantly ($p < 0.05$, 2-tailed, multiple t-tests) elevated over the saline control group levels at each test for the duration of the 60 min. test period (FIG. 1). The magnitude of the increase in vocalization threshold ranged from 60% to 150% over baseline preinjection levels in the VIP 11–28 group, whereas in the saline group, the vocalization threshold showed a $-10\%$ to $-30\%$ change from baseline levels.

VIP 11–28 was also significantly more effective in elevating vocalization thresholds than 25 mcg morphine sulfate ($p < 0.05$, 2-tailed, multiple t-tests) at 1–15, 30 and 60 min. postinjection. This dose of morphine sulfate produced a significant elevation in vocalization threshold over the saline group at 20 and 30 min. post injection. Hence, at 30 min., the elevation in vocalization threshold produced by the VIP 11–28 25 mcge dose (170%) was significantly greater than that produced by the morphine sulfate 25 mcg dose (60%), while both substances produced a significant elevation in vocalization threshold over the saline control group at this time. Thus, VIP 11–28 (25 mcge) was significantly ($p < 0.05$, 2-tailed, multiple t-tests) more effective in elevating vocalization thresholds than a seven-fold greater molar concentration of morphine.

It is also important to note that the significant threshold elevating effect of the fragment persisted through the 60 min. test, at least 30 min. longer than the analgesia produced by the parent compound, VIP 1–28.

Tail Flick Latency (TFL) Test (n = 10)

VIP 11–28 (25 mcge) produced an elevation in TFL of 50%–100% over the preinjection baseline levels, that was significantly ($p < 0.05$, 2-tailed, multiple t-tests) greater than the change in the saline group (0–5%) at the same test periods (FIG. 2). The morphine sulfate (25 mcg and 5 mcg) groups both showed significant elevations in TFL by 15 min. postinjection, ranging from 100% to 350% and persisting for the 60 min. test period. The elevation in TFL produced by VIP 1–28 ranged from 50% to 60% and approached, but did not reach, significance by comparison with the saline group.

Intravenous Injection of VIP 11–28 (n = 10)

VIP 11–28 (3 mg) was injected via a chronically-indwelling intravenous catheter in the jugular vein. This dose was extrapolated from the analgesia-producing dose of 15 mcg (=25 mcge) VIP 11–28 administered intrathecally on the basis that for morphine sulfate, analgesia can be obtained via the intrathecal route at approximately 1/200 the systemic dose (Yaksh, 1986). (For example, a standard dose of morphine sulfate=10 mg/kg=approx. 3 mg systemically in an adult rat=approx. 15 mcg intrathecally.) At this presumably moderate dose of VIP 11–28, the TFL was significantly elevated ($p < 0.05$, 2-tailed, Scheffe test) over the saline control group at all test points between 1 and 60 minutes postinjection (except at 15 min.) (FIG. 3). At 1 minute after injection of VIP 11–28, the mean TFL elevation reached a maximum of 80% greater than the preinjection baseline level, after which it decreased gradually.

On the vocalization threshold test, the maximum threshold occurred at 1 min. after injection of VIP 11–28, approaching, but not attaining, significance (FIG. 4).

EXAMPLE 2 (VIP 11–22)

The VIP 11–22 is synthesized following the above described procedures. This peptide can also be provided by enzymatic cleavage of intact VIP.

Female Sprague-Dawley rats weighing 250 g are used in the testing. The rats are ovariectomized and implanted surgically through the cisterna magna with an intrathecal catheter (i.t.) (PE 10 polyethylene tubing 7.5 cm length) at least 1 week before testing.

VIP 11–22 (104, 52, 26, 13 or 0 micrograms) dissolved in 5 microliters Ringer's Solution (RS) is injected intrathecally (n's=9–18 rats/group). Tail flick latency (TFL) to radiant heat is determined immediately and at 5, 10, 20, 30, 40 and 60 minutes post i.t. injection. All animals also receive a baseline TFL test immediately prior to the injection. Vocalization threshold (VOC-T) to electrical shock of the tail is determined at the same time points pre- and post-injection. Details of nociceptive threshold determinations are described by Cunningham, S. T., Steinman, J. L., Whipple, B., Mayer, A. D. and Komisaruk, B. R. (1991) *Brain Research*, 559:337–343. Data are analyzed using a 2-way ANOVA (dose×time, 5×7) with subsequent t-tests.

FIG. 5 is a graph showing the resulting data.

On the VOC-T test, at 20, 30, 40 and 60 minutes post i.t. injection, the mean threshold is significantly elevated in the 52 microgram VIP 11–22 group compared to the Ringer's and 13 microgram groups. The 52 microgram group differs significantly from the 26 and 104 microgram groups at 40 minutes post i.t. injection only. No other groups show significant changes in mean VOC-T across time post injection. There are no other significant differences among groups at any time point on the VOC-T test. In addition, there are no significant differences among groups on the tail flick latency test.

Summary of Testing

The peptide fragment, VIP 11-22, produces analgesia on the vocalization threshold test when administered directly to the spinal cord.

The analgesia produced by VIP 11-22 was first seen 20 minutes post i.t. injection and continued throughout the 60 minute testing period. This contrasts with the analgesic effect of VIP 11-28, which began immediately (1 minute) post i.t. injection.

EXAMPLE 3

Peptides VIP 11-23, VIP 11-24, VIP 11-25, VIP 11-26 and VIP 11-27 are also synthesized, following the above described procedures and tested showing analgesic activities in the test animals.

Effective analgesic doses for administration to mammals can be selected by using doses corresponding to the following effective analgesic dose range in rats:

1-100 mg/kg body weight intravenously
10-1000 mcg/kg body weight intrathecally or epidurally Besides inducing analgesia on delivery to the central nervous system, the peptide segments provided herein and analogs and derivatives, and pharmaceutically acceptable salts described above, have one or more other pharmacological actions, such as those actions listed herein above for VIP. In illustration, VIP 11-28 peptide segment has shown smooth muscle relaxant action and other of said peptides provided herein are expected also to have said action.

The peptide can be suitably dissolved in physiological saline (Ringer's solution: 100 ml water contains: NaCi: 860 mg, KCi: 30 mg, $CaCl_2$ dihydrate: 33 mg), for such administration.

It will be suggested to those skilled in the art that these peptide segments may be administered via a variety of routes, including intraperitoneal, intramuscular, subcutaneous, percutaneous, via the mucosa (e.g. vaginal, gastrointestinal, nasal, buccal) intraocular, iontophoretically, via continuous infusion and/or orally; it may be in the form of an aerosol and/or powder (e.g. to be administered by insufflation); it could also be prepared in an emulsion, cream, jelly, tablet, suppository, and/or tampon.

The polypeptide compound is administered directly or indirectly. Direct route means any method by which the compound is administered in such a way that it makes direct contact with the central nervous system, e.g., by injection or insertion directly into the brain, spinal cord, and/or the ventricular-central canal system of the central nervous system, and/or by injection of the compound(s) into the intrathecal and/or epidural space surrounding the central nervous system, etc.

Indirect route means any method by which the compound is delivered to the central nervous system via the circulatory system (blood and/or lymphatic), consequent to being injected, e.g., intravenously, intramuscularly, subcutaneously, and/or to being placed in contact with mucosa and/or other tissues (other than central nervous system tissues) that are permeable to the compound(s), and which tissues are supplied by vasculature that in turn provides entry of the compound(s) into the circulatory system which in turn delivers the compound(s) to the central nervous system. Indirect route includes effective oral administration.

The dose forms can be made using customary pharmaceutical extending agents, diluents, carriers and the like including stabilizers, buffers and like agents customarily used in making pharmaceutically acceptable dose forms.

What is claimed is:

1. A therapeutic process for inducing analgesia by administering to a mammal in need of analgesia a pain alleviating amount of a peptide selected from the group consisting of the following:

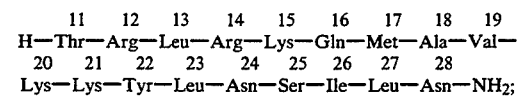

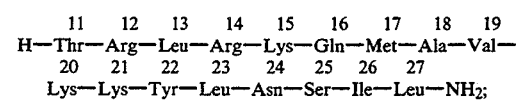

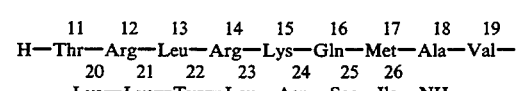

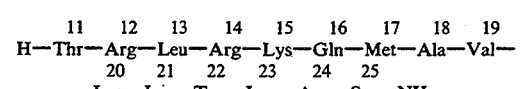

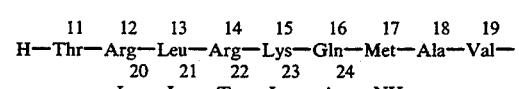

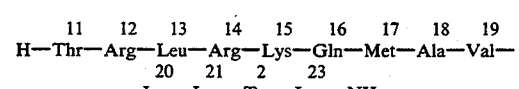

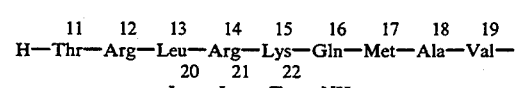

2. A process of claim 1 wherein the amine group of amino acid unit

is a protected amine group.

3. A process of claim 1 wherein the aming group of amino acid unit

is $RHN-TYR-NR_1-$ and R is selected from the group consisting of hydrogen and amine protecting groups and $R_1$ is selected from the group consisting of hydrogen and lower alkyl.

4. A process of claim 1 wherein the peptide is in the form of a pharmaceutically acceptable salt.

5. A process of claim 1 wherein the amine group of amino acid unit

is $RHN-Asp-Asn-Tyr-NR_1-$ and R is selected from the group consisting of hydrogen and amine protecting groups and $R_1$ is selected from hydrogen and lower alkyl.

6. A process of claim 5 wherein the primary amide group of ASN is substituted with $R_2$, a substituent selected from the group consisting of lower alkyl, carbohydrate and N-acetylglucosamine.

7. An analgesic pharmaceutical composition for inducing analgesia and adapted for administration to a mammal in need of analgesia comprising a pain alleviating amount of a peptide selected from the group consisting of the following:

```
  11   12   13   14   15   16   17   18   19
H—Thr—Arg—Leu—Arg—Lys—Gln—Met—Ala—Val—
 20   21   22   23   24   25   26   27   28
Lys—Lys—Tyr—Leu—Asn—Ser—Ile—Leu—Asn—NH2;
```

```
  11   12   13   14   15   16   17   18   19
H—Thr—Arg—Leu—Arg—Lys—Gln—Met—Ala—Val—
 20   21   22   23   24   25   26   27
Lys—Lys—Tyr—Leu—Asn—Ser—Ile—Leu—NH2;
```

```
  11   12   13   14   15   16   17   18   19
H—Thr—Arg—Leu—Arg—Lys—Gln—Met—Ala—Val—
 20   21   22   23   24   25   26
Lys—Lys—Tyr—Leu—Asn—Ser—Ile—NH2;
```

```
  11   12   13   14   15   16   17   18   19
H—Thr—Arg—Leu—Arg—Lys—Gln—Met—Ala—Val—
 20   21   22   23   24   25
Lys—Lys—Tyr—Leu—Asn—Ser—NH2;
```

```
  11   12   13   14   15   16   17   18   19
H—Thr—Arg—Leu—Arg—Lys—Gln—Met—Ala—Val—
 20   21   22   23   24
Lys—Lys—Tyr—Leu—Asn—NH2;
```

```
  11   12   13   14   15   16   17   18   19
H—Thr—Arg—Leu—Arg—Lys—Gln—Met—Ala—Val—
 20   21   22   23
Lys—Lys—Tyr—Leu—NH2;
```

```
  11   12   13   14   15   16   17   18   19
H—Thr—Arg—Leu—Arg—Lys—Gln—Met—Ala—Val—
 20   21   22
Lys—Lys—Tyr—NH2.
```

8. An analgesic pharmaceutical composition of claim 7 wherein the amino group of amino acid unit $$\underset{-\text{Thr}-}{\overset{11}{}}$$

of the selected peptide is a protected amine group.

9. A therapeutic process for inducing analgesia, by administering to a mammal in need of analgesia, a pain alleviating amount of a peptide having the following structure:

```
  11   12   13   14   15   16   17   18   19
H—Thr—Arg—Leu—Arg—Lys—Gln—Met—Ala—Val—
 20   21   22   23   24   25   26   27   28
Lys—Lys—Tyr—Leu—Asn—Ser—Ile—Leu—Asn—NH2
```

10. A therapeutic process for inducing analgesia, by administering to a mammal in need of analgesia, a pain alleviating amount of a peptide having the following structure:

```
  11   12   13   14   15   16   17   18   19
H—Thr—Arg—Leu—Arg—Lys—Gln—Met—Ala—Val—
 20   21   22
Lys—Lys—Tyr—NH2
```

* * * * *

UNITED STATES PATENT AND TRADEMARK OFFICE
CERTIFICATE OF CORRECTION

PATENT NO. : 5,426,099
DATED : June 20, 1995
INVENTOR(S) : Barry R. Komisaruk, et al.

It is certified that error appears in the above-indentified patent and that said Letters Patent is hereby corrected as shown below:

Under Column 16, line 49 of the patent, the text should read as follows:

"3. A process of claim 1 wherein the amine group of"

Signed and Sealed this

Thirty-first Day of October 1995

Attest:

BRUCE LEHMAN

*Attesting Officer*     *Commissioner of Patents and Trademarks*